US005647367A

United States Patent [19]
Lum et al.

[11] Patent Number: 5,647,367
[45] Date of Patent: Jul. 15, 1997

[54] SCANNING ULTRASONIC PROBE WITH LOCALLY-DRIVEN SWEEPING ULTRASONIC SOURCE

[75] Inventors: Paul Lum, Los Altos; Edward Verdonk, San Jose, both of Calif.

[73] Assignee: Hewlett-Packard Company, Palo Alto, Calif.

[21] Appl. No.: 657,742

[22] Filed: May 31, 1996

[51] Int. Cl.$^6$ ................................................ A61B 8/00
[52] U.S. Cl. .................................................. 128/662.06
[58] Field of Search ..................... 128/660.08, 660.09, 128/660.1, 662.03, 662.06; 73/623, 627, 633

[56] References Cited

U.S. PATENT DOCUMENTS

| | | | |
|---|---|---|---|
| 4,375,818 | 3/1983 | Suwaki et al. | 128/662.06 |
| 4,732,156 | 3/1988 | Nakamura | 128/660.09 |
| 4,794,931 | 1/1989 | Yock. | |
| 4,869,258 | 9/1989 | Hetz | 128/662.06 |
| 4,899,757 | 2/1990 | Pope, Jr. et al. | |
| 5,000,185 | 3/1991 | Yock. | |
| 5,176,141 | 1/1993 | Bom et al. | |
| 5,240,003 | 8/1993 | Lancee et al. | |
| 5,271,402 | 12/1993 | Yeung et al. | |
| 5,398,691 | 3/1995 | Martin et al. | 128/662.06 |
| 5,507,294 | 4/1996 | Lum et al. | |
| 5,509,418 | 4/1996 | Lum et al. | |

OTHER PUBLICATIONS

Judy, et al., Magnetic Microactuation of Polysilicon Flexure Structures, Journal of Microelectromechanical Systems, vol. 4, No. 4, Dec. 1995, pp. 162–169.

Judy, et al. Fabrication Processes for Magnetic Microactuators with Polysilicon Flexures, The 4th International Symposium on Magnetic Materials, Processes, and Devices, Chicago, IL, Oct. 8–13, 1995, 2–page paper.

Judy et al., Magnetic Microactuation of Torsional Polysilicon Structures, The 8th International Conference on Solid–State Sensors and Actuators, Stockholm, Sweden, Jun. 25–29, 1995, pp. 332–335.

Liu, et al., A Micromachined Permalloy Magnetic Actuator Array for Micro Robotics Assembly Systems, The 8th International Conference on Solid–State Sensors and Actuators, and Eurosensors IX, Stockholm, Sweden, Jun. 25–29, 1995, pp. 328–331.

Liu, et al., Out–of–Plane Permalloy Magnetic Actuators for Delta–Wing Control, Proc. IEEE Micro Electro Mechanical Systems, Amsterdam, The Netherlands, Jan. 29–Feb. 3, 1995, pp. 7–12.

Garabedian, et al., Microfabricated Surface Plasmon Sensing System, Sensors and Actuators A, 43 (1994), pp. 202–207.

Guckel, et al., A First Functional Current Excited Planar Rotational Magnetic Micromotor, Proc. IEEE Micro Electro Mechanical Systems, Fort Lauderdale, FL, Feb. 7–10, 1993, pp. 7–11.

Ahn, et al., A Planar Variable Reluctance Magnetic Micromotor with Fully Integrated Stator and Wrapped Coils, Proc. IEEE Micro Electro Mechanical Systems, Fort Lauderdale, FL, Feb. 7–10, 1993, pp. 1–6.

(List continued on next page.)

Primary Examiner—George Manuel

[57] ABSTRACT

An ultrasonic probe for imaging tissues from inside a patient's body cavity is disclosed. The ultrasonic probe includes a housing near to the probe's distal end, an ultrasonic beam emitting assembly having a pivotable part, and a driver for producing a pivotal motion on the pivotable part. The housing has a portion that is acoustically transparent. The pivotable part is movable and is operatively connected to the housing. The pivotable part can either have mounted on it a transducer for emitting ultrasound or a reflector for reflecting ultrasound. In either case, when the pivotable part pivots it sweeps ultrasonic energy over a selected angle. The driver is located near to the transducer such that all driving motions for driving the pivotal motion occur near the distal end of the ultrasonic probe.

24 Claims, 9 Drawing Sheets

OTHER PUBLICATIONS

Richards, et al., Surface–Plasmon Excitation Using a Polarization–Preserving optical Fiber and an Index–Matching Fluid Optical Cell, Applied Optics, vol. 32, No. 16, Jun. 1, 1993, pp. 2901–2906.

Wagner, et al., Microactuators with Moving Magnets for Linear, Torsional or Multiaxial Motion, Sensors and Actuators A, 32 (1992), pp. 598–603.

Pister, et al., Microfabricated Hinges, Sensors and Actuators A, 33 (1992), pp. 249–256.

Ahn, et al., A Fully Integrated Micromagnetic Actuator with a Multilevel Meander Magnetic Core, 1992 IEEE, 0–7803–0456–X/92, pp. 14–18.

Wagner, et al., Microfabricated Actuator with Moving Permanent Magnet, 1991 IEEE, CH2957–9/91/0000–0027, pp. 27–32.

Tang, et al., Electrostatic–Comb Drive of Lateral Polysilicon Resonators, Sensors and Actuators, A21–A23 (1990), pp. 328–331.

Steinbruchel, et al., Mechanism of Dry Etching of Silicon Dioxide, J. Electrochem. Soc.: Solid–State Science and Technology, vol. 132, No. 1, Jan. 1985, pp. 180–186.

Sopori, A New Defect Etch for Polycrystalline Silicon, J. Electrochem. Soc.: Solid–State Science and Technology, vol. 131, No. 3, Mar. 1984, pp. 667–672.

Bergeron, et al., Controlled Anisotropic Etching of Polysilicon, Solid State Technology, Aug. 1982, pp. 98–103.

Mandurah, et al., A Model for Conduction Inpolycrystalline Silicon—Part 1: Theory, IEEE Transactions on Electron Devices, vol. ED–28, No. 10, Oct. 1981, pp. 1163–1170.

Bean, Anisotropic Etching of Silicon, IEEE Transactions on Electron Devices, vol. ED–25, No. 10, Oct. 1978, pp. 1185–1193.

Robbins, et al., Chemical Etching of Silicon, Journal of the Electrochemical Society, vol. 107, No. 2, Feb. 1960, pp. 108–111.

Declercq, A New C–Mos Technology Using Anisotropic Etching of Silicon, IEEE Journal of Solid–State Circuits, vol. SC–10, No. 4, Aug. 1975, pp. 191–196.

Tenney, et al., Etch Rates of Doped Oxides in Solutions of Buffered HF, J. Electrochem. Soc.: Solid–State Science and Technology, vol. 120, No. 8, Aug. 1973, pp. 1091–1095.

Kamins, et al., Diffusion of Impurities in Polycrystalline Silicon, J. Appl. Phys., vol. 43, No. 1, Jan. 1972, pp. 83–91.

van Gelder, et al., The Etching of Silicon Nitride in Phosphoric Acid with Silicon Dioxide as a Mask, J. Electrochem. Soc.: Solid–State Science, vol. 114, No. 8, Aug. 1967, pp. 869–872.

Judy, et al., Batch–Fabricated, Addressable, Magnetically Actuated Microstructures, Solid–State Sensor and Actuator Workshop, Hilton Head, SC, Jun. 2–6, 1996, pp. 187–190.

SCANNING ULTRASONIC PROBE WITH LOCALLY-DRIVEN SWEEPING ULTRASONIC SOURCE

FIELD OF THE INVENTION

The present invention relates to intracavity ultrasonic probes, more particularly, to intracavity ultrasonic probes that scan tissues surrounding the ultrasonic probe by mechanically moving a transducer in the ultrasonic probe.

BACKGROUND

For many diseases, a more accurate diagnosis can be made if an image of the body tissue affected by the disease can be observed. However, many body tissues are not readily observable. Recently, ultrasonic imaging has been widely used for diagnosing diseases in a body cavity, such as in the vascular system, gastrointestinal tract, and the like. This involves inserting an ultrasonic probe into the targeted body area with a catheter. The ultrasonic probe transmits an acoustic pulse into the body and detects the reflections of the pulse at tissue boundaries due to differences in acoustic impedance. The differing times taken for the transducer to receive the reflected pulse correspond to variations in the distance of the tissue boundaries from the ultrasonic source. By stepping, or sweeping, the ultrasonic probe through a selected angle, a two dimensional ultrasound image corresponding to a map of the acoustic impedance boundaries can be obtained. The intensity and position of the reflections from these boundaries will provide information on the condition of the body tissue being imaged.

Generally, there are two types of ultrasonic probes for diagnostic ultrasonic imaging. The first employs a synthetic aperture technique. For example, U.S. Pat. No. 4,917,097 (Proudian et al.) and U.S. Pat. No. 5,186,177 (O Donnell et al.) teach how an ultrasonic beam is steered electronically from a transducer using the method of synthetic aperture. Generally, this involves the sequential excitation of selected elements in an array of transducer elements. The second scans by mechanical rotation of a means to direct acoustic pulses. The mechanically rotated type includes a few subclasses. In the first subclass, either the distal (remote from the operator) transducer or a mirror is rotated from the proximal end of the catheter by an extended drive shaft with a proximal motor (U.S. Pat. No. 4,794,931 (Yock) and U.S. Pat. No. 5,000,185 (Yock)). In the second subclass, the rotation is confined to the distal end, where either a miniature motor (U.S. Pat. No. 5,240,003 (Lancee et al.) and U.S. Pat. No. 5,176,141 (Bom et al.)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide that conducts the sound to the distal end (e.g., U.S. Pat. No. 5,284,148 (Dias and Melton). In another subclass, e.g., U.S. Pat. No. 5,509,418 (Lure et al.), a turbine is rotated by an acoustic signal generated outside the vascular vessel to direct another ultrasonic signal in a rotating fashion. In yet another subclass, e.g., U.S. Pat. No. 5,507,294 (Lum et al.), an external driving member rotates a tube to rotate a reflecting element at the tip of the tube to reflect ultrasound.

Currently, the most widely used type of intracavity ultrasonic probe is the mechanically rotated system with a transducer having a single planar element placed at the distal end of the catheter. A reason for this preference is the superior image quality as compared with current synthetic aperture systems. However, the mechanically rotating ultrasonic probes have some shortcomings. For an ultrasonic probe with a drive motor proximal to the operator, i.e., remote from the transducer, a drive cable encircled by a sheath is generally needed to transfer mechanical energy to the tip of the catheter containing the transducer. A long cable may not transfer energy uniformly to the catheter tip to rotate the transducer or reflector uniformly. Furthermore, the probe is liable to fail over time because of the cable's rapid and repetitive rotation within the sheath. On the other hand, when a drive motor is located near the tip of the catheter, the motor must be small. Such fragile motors are electrically and mechanically complex, making them very expensive. With mechanical parts, e.g., ball bearings, etc., that undergo rigorous motion, the motor is liable to fail. What is needed is an ultrasonic probe with a structurally simple actuator at the tip of the catheter for moving a transducer to scan tissues.

SUMMARY

The present invention provides an ultrasonic probe for imaging tissues from inside a patient's body cavity. The ultrasonic probe is elongated and has a distal end suitable for inserting inside the body cavity. The proximal end of the ultrasonic probe remains outside the body.

The ultrasonic probe includes a housing proximate to the ultrasonic probe's distal end, an ultrasonic-beam-emitting assembly having a pivotable part and a driver for producing a pivotal motion on the pivot able part. The housing has a portion that is acoustically transparent. The pivot able part is movable and is operatively connected to the housing, i.e., the pivot able part may be connected indirectly to the housing, for example, via an electromagnet. The pivot able part can either have mounted on it a transducer for emitting ultrasound or a reflector for reflecting ultrasound from an ultrasound source. In either case, when the pivot able part pivots it sweeps ultrasonic energy over a selected angle. The driver is located proximate to the transducer such that all driving motions for driving the pivotal motion occur proximate to the distal end of the ultrasonic probe.

In the ultrasonic probe of the present invention, a cable is no longer needed to transfer rotational energy from the proximal end to the distal end of the ultrasonic probe as in the prior art devices. In fact, no energy needs to be transferred mechanically from the proximal end to the tip of the ultrasonic probe. The ultrasonic probe of the present invention can be advantageously used for imaging tissues in a body cavity, for example, within a blood vessel. The imaging is done by scanning an acoustic beam of ultrasonic pulses over the tissues by a pivotal motion of a platform on which a transducer is affixed. As the platform pivots, the transducer, mounted on the platform, wobbles back and forth, thus sweeping the acoustic beam over a selected angle. Preferably, the platform pivots on a fulcrum at about the midpoint of the platform in a rocking (or see-sawing) manner. In the preferred apparatus the fulcrum is a torsion arm that is twistable to allow the platform to pivot. Therefore, no mechanical sliding, rolling, or frictional motion exists. This reduces the risk of failure of the ultrasonic probe.

Moreover, unlike motorized ultrasonic probes, the electromechanical system used to drive the pivotal motion in the present invention is relatively simple. No sophisticated stator and rotor mechanism is required at the distal end of the ultrasonic probe where the transducer is located. Therefore, a small driver, used for actuating the pivotal motion, can be fabricated with enhanced reliability for the ultrasonic probe. This will enable the fabrication of an ultrasonic probe usable in even small blood vessels or body cavities. Both forward-looking and sideward-looking transducers can be implemented in the same ultrasonic probe. This obviates the need for multiple instrument exchanges if both forward looking and sideward looking capabilities are required, thereby reducing the time needed for the imaging process and the trauma resulting from maneuvering the catheter within the body.

BRIEF DESCRIPTION OF THE DRAWINGS

The following figures show the embodiments of the present invention to better illustrate the apparatus of the present invention. In these figures, like numerals represent like features in the several views and the drawings are not drawn to scale for the sake of clarity.

DETAILED DESCRIPTION OF THE INVENTION

The present invention provides an ultrasonic probe that has an actuating mechanism proximate to the probe's tip, which is insertable into a patient's body. With the actuating mechanism at the tip, a long mechanical-energy-transferring system for transferring energy from a motor or a similar mechanical actuator outside the body is obviated. Thus, there is no need for cumbersome features such as cables for mechanically turning the transducer in a sheath.

Figure 1:
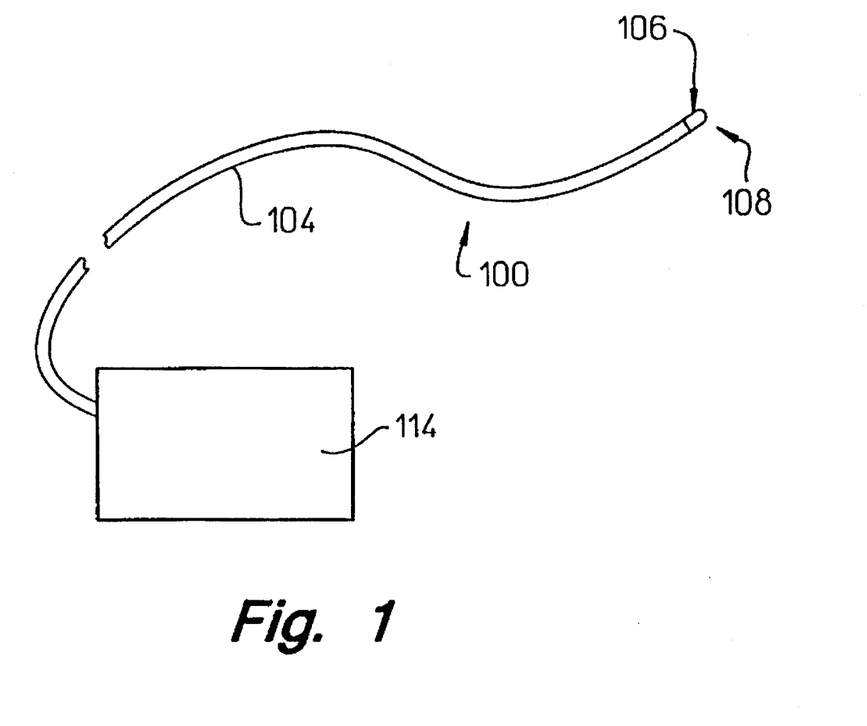
FIG. 1 shows a schematic representation of an ultrasonic probe according to the present invention.

An exemplary ultrasonic probe 100 of the present invention is schematically shown in FIG. 1. The ultrasonic probe 100 has an elongated body 104 connected to an "imaging head" 106 at the ultrasonic probe's distal end 108. As used herein, the term "distal" end of the ultrasonic probe refers to the end that can be inserted into a patient's body cavity, e.g., the lumen of a blood vessel. As used herein, the term "body cavity" refers to a hollow area generally surrounded by walls, although the hollow area is not necessarily entirely enclosed. Further, it is not limited to readily accessible cavities such as the oral cavity, the rectum, and the like. In the following description, a blood vessel is used as an example for the body cavity in which the ultrasonic probe can be used. However, it is to be understood that the present invention can be adapted for use in a variety of body cavities, such as a chamber in the heart, esophagus, stomach, intestine, abdominal cavity, bladder, uterus, and the like.

Figure 2:
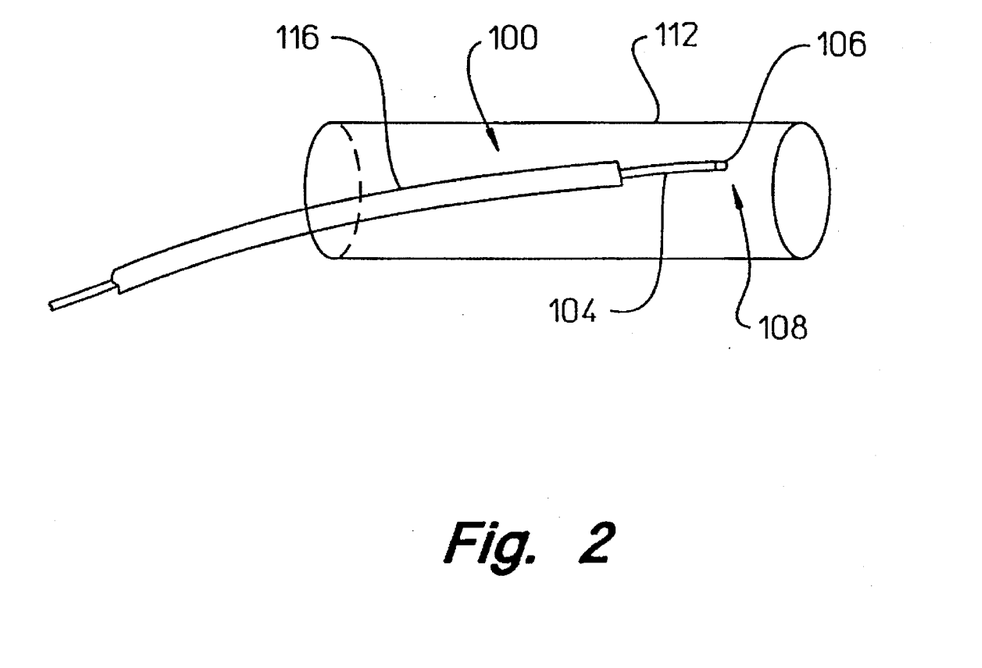
FIG. 2 shows a schematic representation of an ultrasonic probe according to the present invention, showing the probe being deployed in a blood vessel.

FIG. 2 shows how the ultrasonic probe 100 is deployed in a blood vessel 112. The imaging head 106 contains an ultrasound-emitting assembly which includes a transducer and the actuating mechanism for moving the transducer to scan an ultrasonic beam in the blood vessel 112. The ultrasonic beam is consisted of pulses. The proximal end, which is remote to the distal end 108, is electrically connected to an ultrasound controller 114 (see FIG. 1) that controls the emission and reception of ultrasound, as well as steering the ultrasound-emitting assembly. This controller 114 can also have the capability to analyze the electronic signals transmitted from the ultrasonic probe as a result of ultrasound signals received by the imaging head 106. Preferably, the controller 114 can further store and display data. In this case, computers, CRT monitors, and the like, can be present in the controller 114. An elongated sheath 116 surrounds a significant portion of the elongated body 104 of the ultrasonic probe 100. The sheath is used to facilitate the insertion of the ultrasonic probe 100 into the blood vessel 112.

Figure 3A:
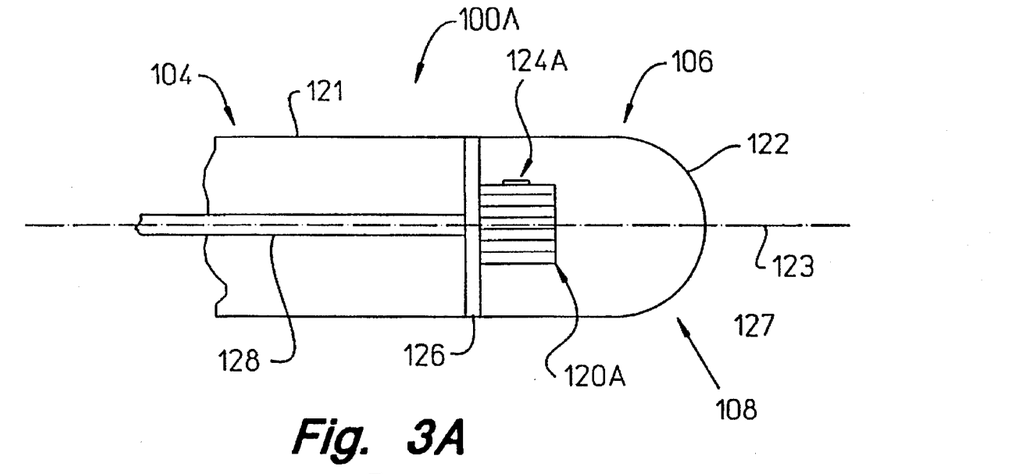
FIG. 3A shows a schematic representation of an embodiment of an ultrasonic probe according to the present invention.
Figure 3B:
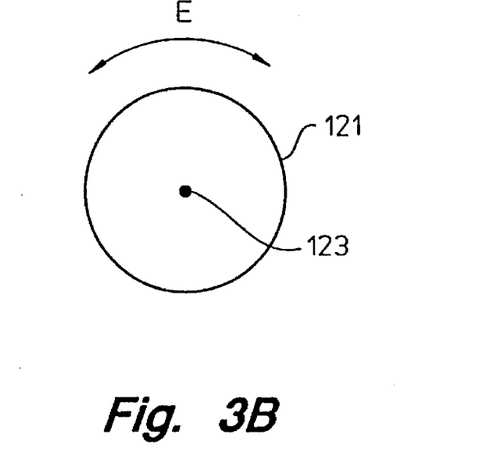
FIG. 3B is a schematic representation in axial view of the an embodiment according to FIG. 3A illustrating the direction of pivoting.
Figure 3C:
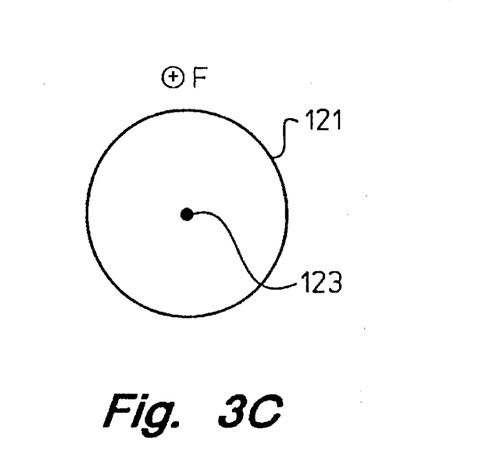
FIG. 3C is a schematic axial representation in axial view of the another embodiment according to FIG. 3A illustrating the direction of pivoting.

FIG. 3A shows further details of a portion of an embodiment of the ultrasonic probe (labeled as 100A in FIG. 3A) at the distal end 108. In this embodiment, the elongated body 104 of the ultrasonic probe 100A is a catheter 121 that is connected to the imaging head 106. The imaging head 106 has a housing 122, for enclosing and protecting a microactuator 120A with a pivot able transducer assembly 124A for emitting and receiving ultrasonic signals. The housing 122 is acoustically transparent to ultrasound emitted by the transducer assembly 124A. Alternatively, the housing 122 can have a window for emitting and receiving ultrasound. A support 126 is located proximal to and supports the microactuator 120A in rigid relation to the housing 122 and the catheter 121. The ultrasonic probe has a center line extending longitudinally along the elongated body 104. The center line of the ultrasonic probe near the imaging head 106 is essentially a straight line and coincides with the longitudinal axis 123 of the distal portion of the ultrasonic probe 100A. The transducer 144 (see FIG. 6) is located laterally from the microactuator 120A. As used herein, "laterally" refers to a positional relationship in a direction radial to the axis 123 of the ultrasonic probe. A liquid 127 is contained in the housing 122. The liquid 127 matches the ultrasonic impedance of the housing 122 to reduce reverberations that damp the pivoting action of the microactuator 120A. The support 126 can also forms a liquid-tight seal with the housing 122 to contain the liquid, although it can also be nonliquid-tight so as to allow infusion of fluid from the proximal end to the chamber defined by the housing 122. The transducer assembly 124A is generally planar and its normal points generally perpendicularly to the axis 123 of the ultrasonic probe 100A. As the transducer assembly 124A emits an ultrasonic beam, the microactuator 120A rocks the transducer assembly 124A to sweep the ultrasonic beam in a plane perpendicular to the axis 123, as shown in FIG. 3B. The sweeping motion of the ultrasonic beam is shown by the two-headed arrow E. In an alternative embodiment, the transducer and the microactuator are arranged such that the ultrasonic beam sweeps out a plane parallel to the axis 123. The sweeping path of the ultrasonic beam is shown by the symbol ⊕, marked by F, going into the page in FIG. 3C. The wires for exciting the transducer on the transducer assembly 124A and the microactuator are located along a cable 128 in the catheter 121 (see FIG. 3A).

Figure 4:
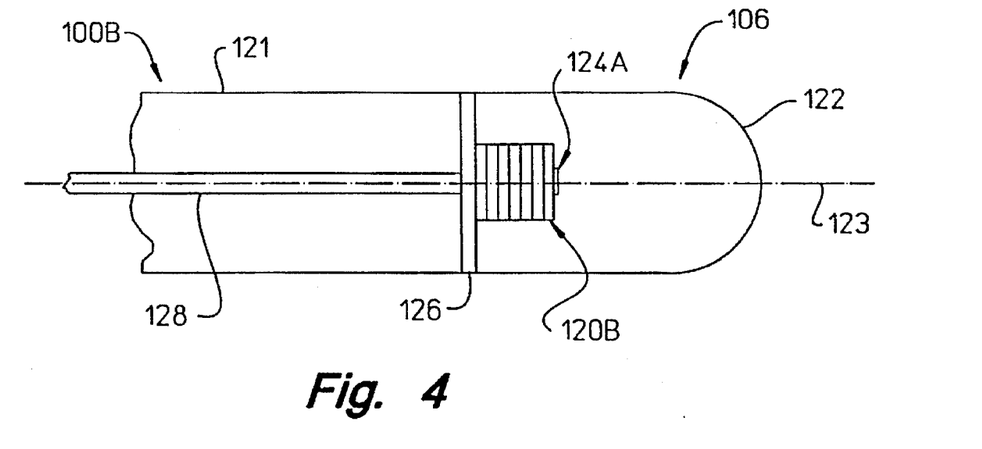
FIG. 4 shows a schematic representation of another embodiment of an ultrasonic probe according to the present invention.

In another embodiment of the ultrasonic probe of the present invention, the distal portion of which is shown in FIG. 4, the transducer in the transducer assembly 124B is affixed distally to the microactuator 120B, thereby providing a way to scan axially, i.e., the scan angle can have a median generally along the axis 123 of the ultrasonic probe.

Figure 5:
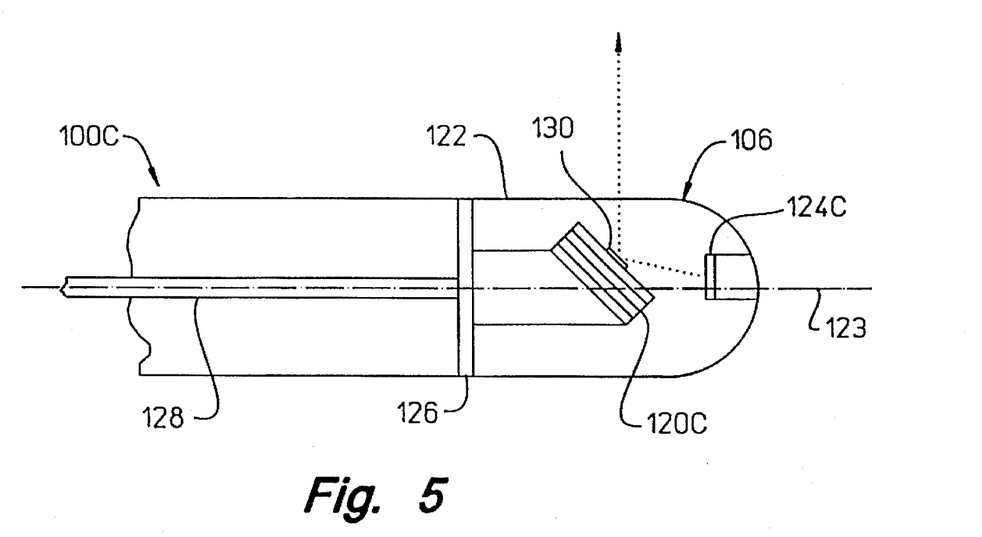
FIG. 5 shows a schematic representation of an embodiment of yet another ultrasonic probe according to the present invention.

In yet another embodiment of an ultrasonic probe, shown in FIG. 5, a transducer assembly 124C is supported proximate to the distal end 108 of the ultrasonic probe 100C along the probe's axis 123. A transducer 124C emits an ultrasonic beam axially toward the proximal end. The microactuator 120C and a pivot able reflector 130 are mounted at a slanted angle to the axis 123 of the ultrasonic probe such that the reflector reflects the axially-directed ultrasonic beam in a radial direction. As the reflector 130 pivots, it sweeps the ultrasonic beam to locations lateral to the ultrasonic probe 100C, thereby scanning the wall of the blood vessel 112 lateral to the ultrasonic probe.

Figure 6:
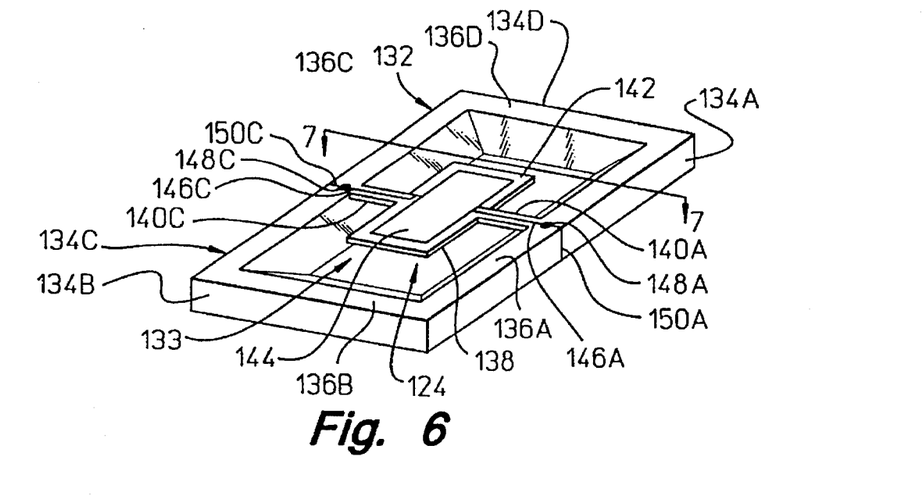
FIG. 6 shows an isometric representation of an embodiment of an ultrasonic probe according to the present invention, showing the transducer in a slab-shaped stage.
Figure 7:
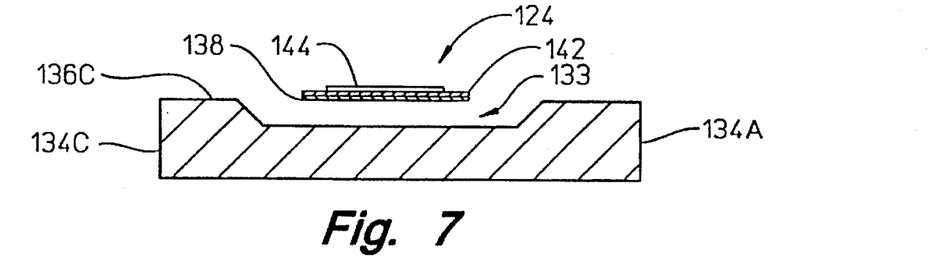
FIG. 7 shows a sectional view along line 7—7 of FIG. 6.

FIG. 6 shows a stage 132 of the ultrasonic probe according to the present invention in more detail. FIG. 7 shows a sectional view of the stage 132 along the line 7—7 in FIG. 6. In this embodiment, the stage 132 is generally slab-shaped. As used herein, the term "stage" refers to the structure that includes the substrate, platform, torsion arms, magnetic material, and the transducer, which will be described below. A cavity 133 in the stage 132 is surrounded by walls 134A, 134B, 134C, 134D, on which are ledges 136A, 136B, 136C, 136D. A generally rectangular platform 138 is supported on two opposing ledges 136A, 136C by two torsion arms 140A, 140C, one located about the mid point of each opposite edge of the stage 132. The platform 138 is balanced on the torsion arms 140A, 140C with the platform's center of gravity on an imaginary line joining the torsion arms. In this way, a minimal effort is needed to pivot, or turn, the platform on the torsion arms. If desired, the platform's center of gravity can be slightly off the torsion arms 140A, 140C without significantly affecting the performance of the ultrasonic probe. As used herein, the term "transducer assembly" refers to the structure including the platform, transducer, and magnetic material, if any. The terms "pivot" and "pivotal," when referring to moving the platform or transducer assembly, describes the turning motion about supporting arms that pivot or turn as if in a pivot. Therefore, the twisting motion on torsion arms, as long as the platform or transducer assembly is observed to turn or swing as if it is on a hinge or on a pivot, is considered to be "pivotal." Because the torsion arms 140A, 140C are affixed to the walls of the stage 132, the platform 138 pivotally moves in a rocking fashion, thereby enabling a sweeping scan by the transducer affixed on the platform.

A magnetic material 142, e.g., a nickel ferrite (herein referred to as "NiFe") material, is layered on a surface of the platform 138, covering generally all of that surface. In this way, when a varying magnetic field is applied to the platform, the platform will pivot on the torsion arms instead of trying to move up and down as a whole. Due to the ease of fabrication, preferably, the magnetic material 142 is layered on the upper surface of the platform 138. As used herein, the "upper" surface refers to the surface that faces away from the cavity 133. If preferred, the magnetic material can be layered on the upper surface of the platform 138 on only one side of the torsion arms 140A, 140C, covering half of the surface.

The transducer assembly 124 includes the magnetic material 142 and a transducer 144 mounted on the upper surface of the platform 138. Electrical wires 146A, 146C extend from transducer electrodes (not shown in the figures) to connection pads 148A, 148C. The connection pads 148A, 148C in turn can be connected to electrical wires 150A, 150C to provide electrical energy to the transducer 144. Alternatively, one or more of the wires 146A, 146C, 150A, 150C can be replaced by appropriately doped channels in the torsion arms and frame of the stage, i.e., stage 132. The electrodes are connected to the surfaces of the transducer 144 to electrically generate and receive ultrasound by the piezoelectric effect. As the transducer 144 is excited and the platform 138 is pivoted by a varying magnetic field, the transducer radiates an ultrasonic beam to scan tissues in the blood vessel normal to the planar surface of the transducer.

Figure 8:
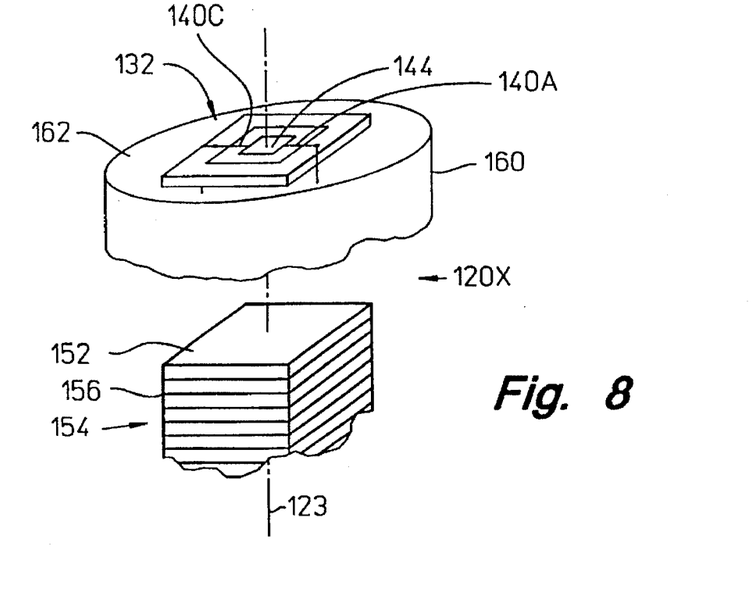
FIG. 8 shows an exploded view in portion of the microactuator of an ultrasonic probe according to the present invention, showing an electromagnet.
Figure 9A:
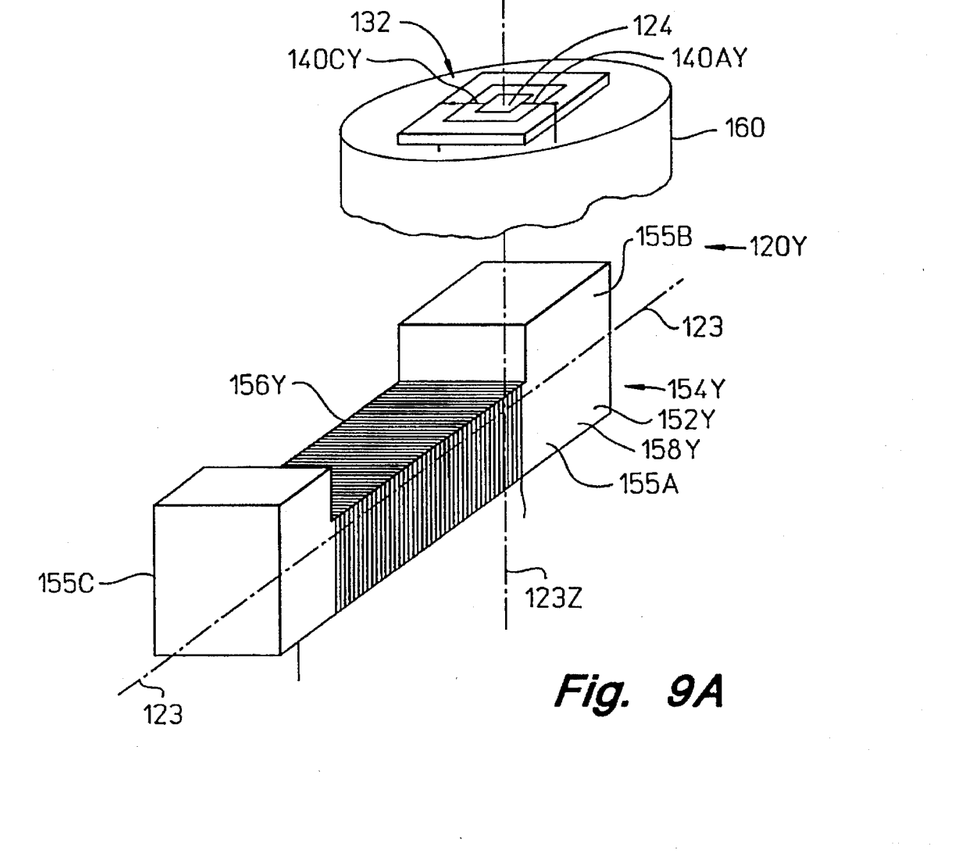
FIG. 9A shows an exploded view in portion of the microactuator of another ultrasonic probe according to the present invention, showing an electromagnet.

FIG. 8 is an exploded view showing how the microactuator is located relative to the transducer. The microactuator 120X can be considered to include the stage 132 having the platform 138 (see FIG. 7) and torsion arms 140A, 140C, as well as the magnetic material 142 layered on the platform. The transducer assembly 124 is moved by the pivotal movement of the platform 138 about the torsion arms 140A, 140C caused by variations of a magnetic field in which the magnetic material is situated. An electromagnet 154 is proximate to the stage 132 to provide the varying magnetic field. The electromagnet 154 contains a coil 156 that is wrapped around a core 152. An electrical current can be passed through the coil 156 to produce a varying magnetic field. The core 152 of the electromagnet 154 extends parallel to, preferably along, the axis 123 of the ultrasonic probe. This means that a long core can be used to increased the number of turns of the coil, since the length of the electromagnet can extend along the axis 123 and is not limited by the diameter of the ultrasonic probe in this embodiment. Such an actuator is suitable for use in an ultrasonic probe similar to that shown in FIG. 4. The coil 156 is wrapped such that the axis of the coil is perpendicular to the plane of the stage 132 and the platform 138 is located generally at about the axis of the coil, which is parallel to the axis 123 of the ultrasonic probe. In this way, the lines of the magnetic field pass through the platform 138 in a direction generally perpendicular to the plane of the stage 132. The stage 132 can be affixed to the electromagnet 154 by commonly known affixing means, such as adhesive, clips, clamps, and the like. Optionally, a tube 160 with an end plate 162 can be used to anchor and protect the stage 132 and the electromagnet 154. It is noted that if a short core is used so that the electromagnet and the stage 132 can fit transversely inside the imaging head 106, this arrangement of arranging the platform 138 with the electromagnet 154 is also applicable for an ultrasonic probe of FIG. 3A FIG. 9A shows an exploded view of another embodiment of a transducer assembly and a microactuator that is especially suitable for an ultrasonic probe of FIG. 3A. In this embodiment, the stage 132 is generally similar to the stage 132 of FIG. 8. The electromagnet 154Y has a U-shaped core 152Y. The core 152Y has an elongated core body 155A with a first leg 155B and a second leg 155C extending about perpendicularly from its ends. The first leg 155B is more distal than the second leg 155C in the ultrasonic probe. A coil 156Y is wrapped around the core 158Y. The axis of the coil is generally parallel to the axis 123 of the ultrasonic probe so that a long electromagnet can be used. The stage 132 is proximate to and preferably rests on the first leg 155B at the distal end of the ultrasonic probe. In this way, the lines of the magnetic field in the electromagnet 154Y are channeled from the elongated core body 155A and pass out of the first leg 155B through the stage 132. Thus, as the current passing through the coil 156Y varies, the electromagnet's magnetic field varies and pivots the platform on the torsion arms 140AY and 140CY. Again, as in FIG. 8, the electromagnet 154Y can be positioned proximate to or affixed to the stage 132. An alternative to a U-shaped core is a L-shaped core, which still allows the stage 132 to be placed on the leg at the distal end of the core. The electromagnet with a U-shaped core or a L-shaped core can also be used in an ultrasonic probe of FIG. 5.

Figure 9B:
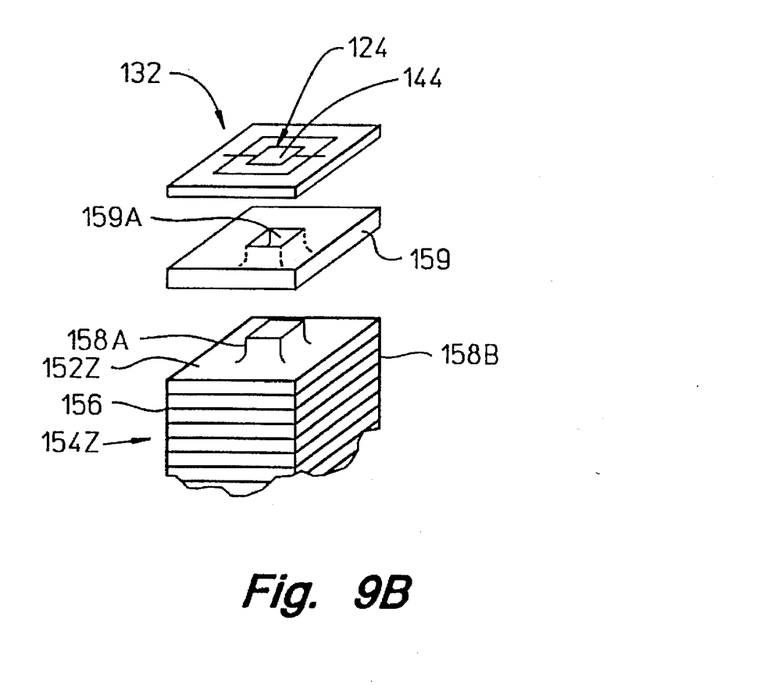
FIG. 9B shows an exploded view in portion of the microactuator of another ultrasonic probe according to the present invention, showing an electromagnet with a core having a finger.

The strength of the electromagnet can be increased by increasing the number of loops in the coil, increasing the cross sectional area of the magnetic core (and therefore the size of the loops), and increasing the current in the coil. Since the platform 138 (see FIG. 7 and FIG. 14) is small and only magnetic field lines passing through the magnetic material on the platform affect the pivotal motion, as shown in FIG. 9B in portion, to increase the effective magnetic field strength, the electromagnet 154Z can have a magnetic core 152Z including a finger 158A extending from a larger body 158B. The larger body 158B of the magnetic core allows the coil 156 to have larger loops. At the finger 158A, the magnetic field lines are concentrated to pass through the magnetic material on the platform 138. Preferably, a spacer 159 having a void 159A for receiving the finger 158A can be disposed between the larger body 158B of the core and the stage 132 to help secure the stage to the electromagnet 154Z. The spacer 159 can have planar dimensions generally similar to those of the stage 132.

With the above-described arrangements, the stage 132 and the electromagnet can be enclosed in the imaging head 106 without enlarging the radial dimension of the imaging head. Methods of making coils and electromagnets for microactuators are known in the art. Some methods involve using a metallic coil, e.g., by deposition, and some involve doping a silicon material to form the conductive coil for the electromagnet. See, e.g., Wagner et al., "Microactuators with Moving Magnets for Linear, Torsional or Multiaxial Motion," *Sensors and Actuators*, A. 32, 1992, pp. 598–603; Kamins, et al., "Diffusion of impurities in Polysilicon," *J. Appl. Phys.*, 43(1), January 1972, p. 83–91; Mandurah, et al., "A Model for Conduction in Polycrystalline Silicon, Part 1: Theory," *IEEE Trans. of Electron Devices*, Vol. ED-28, No. 10, October 1981, p. 1163–1170; whose descriptions of the methods for doping and for fabricating a microactuator are incorporated by reference herein.

In another embodiment, more than one transducer can be present in the imaging head 106. In fact, more than one stage, each positioned such that the transducer thereon directs an ultrasonic beam at a different direction, can be present. This can be done, for example, by combining the transducer assemblies of FIG. 3A and FIG. 4.

Method of Making the Apparatus

The microactuator and the transducer assembly can be made by micromachining methods known in the art, e.g., Judy and Muller, "Magnetic Microactuation of Torsional Polysilicon structures," *Dig. Int. Conf. Solid-State Sensors and Actuators*, Stockholm, Sweden, Jun. 25–29, 1995, pp. 332–339; Ahn and Allen, "A Fully Integrated Micromagnetic Actuator with a Multilevel Meander Magnetic Core," *Tech. Dig. IEEE Solid-State Sensor and Actuator Workshop*, (Hilton Head '92), Hilton Head Island, S.C., Jun. 22–25, 1992, pp. 14–18; Liu et al., "Out-of-Plane Permalloy Magnetic Actuators for Delta-Wing Control," *Proc. IEEE Micro Electro Mechanical Systems (MEMS'95)*, Amsterdam, The Netherlands, Jan. 29–Feb. 2, 1995, pp. 7–12; Judy and Muller, "Magnetic Microactuation of Polysilicon Flexure Structures," *J. Microelectromechanical Systems*, 4(4), December 1995, pp. 162–169; and Pister et al. "Microfabricated Hinges," *Sensors and Actuators*, A. 33, 1992, pp. 249–256, of which the description on methods of making microactuators are incorporated by reference herein.

FIGS. 10 to 14 show how such micromachining can be done using a silicon substrate; a sacrificial layer made of, e.g., silicon dioxide ($SiO_2$) or glass; a platform and torsion arms made of, e.g., polysilicon or silicon nitride ($Si_3N_4$); and on the platform a layer of magnetic material, e.g., nickel ferrite (herein referred to as NiFe) permalloy consisting of 80% nickel and 20% iron. In scientific literature, this material with 80% nickel and 20% iron is sometimes represented by $Ni_{80}Fe_{20}$. It is noted that other magnetic materials can also be used, as long as it can be attracted by the electromagnet to pivot the platform. Briefly, a substrate with a thickness about the desired thickness of a stage 132 is provided. A layer 170 of sacrificial material, e.g., silicon dioxide, is deposited on the substrate 168, followed by a grown fill 172 of either polysilicon or silicon nitride. The layer of magnetic material, e.g., NiFe, is deposited on the polysilicon or silicon nitride layer. Then, through appropriate masking and etching techniques, selected portions of the magnetic material (e.g., NiFe 178), seed layer 174, platform material, and sacrificial layer 170 are removed to form the platform 138 and torsion arms 140A, 140C. Methods of forming such suitable layers of substrate 168, sacrificial material 170, platform material 172, and magnetic material (e.g., NiFe 178) are known in the art. Further selective etching of the silicon substrate 168 will allow the formation of a cavity 133.

An alternative to polysilicon or silicon nitride is polyimide, e.g., PI-2611 from DuPont Company (Wilmington, Del.). A polyimide layer is typically formed by spinning. Such a layer can be etched by dry plasma etching. Polyimide materials suitable for such applications are available commercially from chemical suppliers such as DuPont Company and Ciba Geigy Corp. (Greensboro, N.C.). Methods of spinning and etching a polyimide layer are known in the art. See, e.g., Ahn, et al., "A Planar Variable Reluctance Magnetic Micromotor with Fully Integrated Stator And Wrapped Coils," *Proc. IEEE Micro Electro Mechanical Systems (MEMS'93)*, Fort Lauderdale, Fla., Feb. 7–10, 1993.

To illustrate the method of forming the stage 132 of the present invention, an embodiment that includes a silicon substrate layer, a $SiO_2$ sacrificial layer, a silicon nitride platform with torsion arms, and a magnetic material layer of NiFe is described below. It is commonly known that glass and $SiO_2$ can be etched with suitable chemicals, e.g., buffered hydrofluoric acid (HF) mixtures; silicon can be etched with potassium hydroxide (KOH); glass, $SiO_2$, polysilicon, and silicon nitride can be dry-etched with plasma chemistry known to one skilled in the art; and silicon nitride can also be wet-etched with phosphoric acid ($H_3PO_4$). It is also known that these etching methods affect each material (e.g., Silicon, silicon nitride, polysilicon, $SiO_2$, NiFe) differently. This difference is due to the materials' inherent physical and chemical properties. The different etch rates for such materials using a wide variety of etchants will allow the ability to etch differentially one material quickly and another very slowly.

Figure 10:
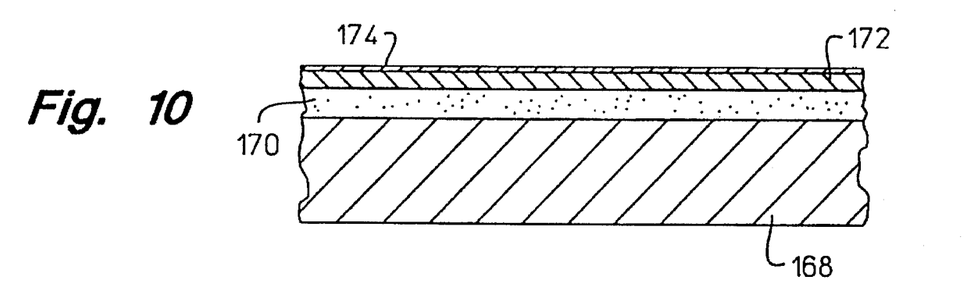
FIG. 10 shows a sectional view of layers of material during the formation of an embodiment of a stage in the fabrication of the microactuator of an ultrasonic probe according to the present invention.

As an example, layers of materials shown in FIG. 10, including silicon nitride 172, $SiO_2$ 170, and silicon 168, but less the conductive seed film 174, can be considered. The Silicon nitride layer 172 can be lithographically masked and patterned with hot $H_3PO_4$ at about 50° C. The acid will etch completely through the exposed silicon nitride areas relatively quickly but the etch rate will slow down considerably, i.e., in orders of magnitude, on the exposed $SiO_2$ layer 170. The lithographic masking material on top of the silicon nitride layer can be removed by an oxygen plasma with minimal effect on the exposed $SiO_2$ layer 170. Neither will the oxygen plasma affect the exposed silicon nitride layer. At this stage of the process, the lithographic masking material on the silicon nitride has been removed and the opening in the silicon nitride layer exposes a thin layer of $SiO_2$. A brief characterized timed dip, e.g., of about 10 seconds, in a 10:1 hydrofluoric acid will remove the exposed $SiO_2$ layer 170. The final silicon substrate 168 is now exposed. A final KOH etch can be used to isotropically etch the silicon substrate 168. The proper dilutions at the proper temperature will minimally affect the $SiO_2$ layer 170 and the silicon nitride layer 172. Proper timed exposure of the materials to hot KOH will result in a silicon etched cavity approximately defined by the silicon nitride 172 and $SiO_2$ 170 opening. This general process methodology will be applied to fabricate the structures of interest.

Etching methods for various materials are known in the art. For example, methods for etching silicon dioxide are described in Steinbruchel et at., "Mechanism of dry etching of silicon dioxide—A case study of direct reactive ion etching," *J. Electrochem. Soc. Solid-state and Technology*, 132(1), pp. 180–186, January 1985; and Tenney et al., "Etch Rates of Doped Oxide in Solutions of Buffered HF," *J. Electrochem. Soc. Solid State and Technology*, 120(8), pp. 1091–1095, August 1973. Polysilicon etching is described by Bergeron et al., "Controlled Anisotropic Etching of Polysilicon," *Solid State Technologies*, August 1982, pp. 98–103; and B. L. Sopori, "A New Defect Etch for Polycrystalline Silicon," *J. Electrochem. Soc. Solid State and Technology*, 131(3), pp. 667–672, March 1984. Silicon Nitride etching is described by van Gelder et al., "The etching of Silicon Nitride in Phosphoric Acid with Silicon Dioxide as a mask", *J. Electrochem. Soc. Solid State and Technology*, 114(8), August 1967, pp. 869–872. Silicon etching is described by M. J. Declercq, "A New CMOS Technology Using Anisotropic Etching of Silicon," *IEEE J. of Solid State Circuits*, Vol. SC-10, No. 4, August 1975, pp. 191–196; K. E. Bean, "Anisotropic Etching of Silicon," *IEEE Trans. Electron. Devices*, Vol. ED-25, No. 10, October 1978, pp. 1185–1193; and Robbins, et al., "Chemical Etching of Silicon II. The system of HF, $HNO_3$, $H_2O$, and $HC_2H_3OO_2$," *J. Of The Electrochemical Society*, 107(2), February 1960, pp. 108–111.

As an illustrative example to form a platform with a transducer, as shown in FIG. 10, a $SiO_2$ sacrificial layer 170 of a desired shape, size, thickness, and pattern is formed on a silicon substrate 168. The sacrificial layer 170 is covered with a $Si_3N_4$ layer 172. This $Si_3N_4$ layer 172 is then covered with a photoresist, masked, and etched to form the desired size, shape, and pattern suitable to support the magnetic material and the transducer and to withstand the rigor of repeated torsional mining of the torsional arms during operation. A conductive seed film 174, e.g., containing a chromium film and a copper film, is then vapor deposited on the selected surface on the $Si_3N_4$ layer 172 to facilitate the deposition of the magnetic material.

Figure 11:
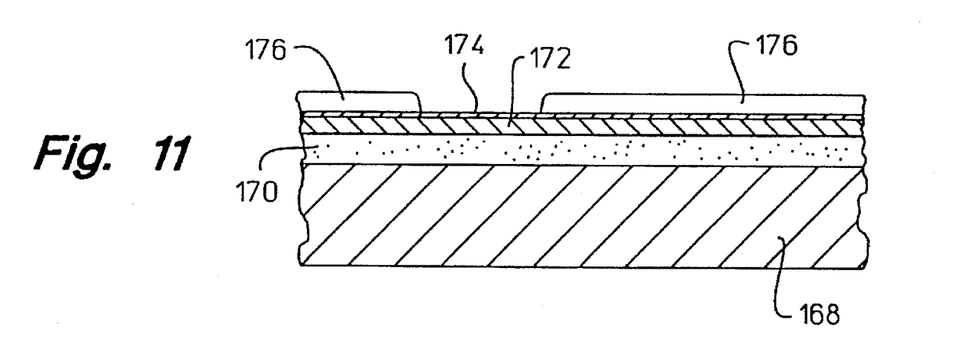
FIG. 11 shows a sectional view of layers of material during the formation of an embodiment of a stage in the fabrication of the microactuator of an ultrasonic probe according to the present invention, showing the preparation of patterning a layer of magnetic material.
Figure 12:
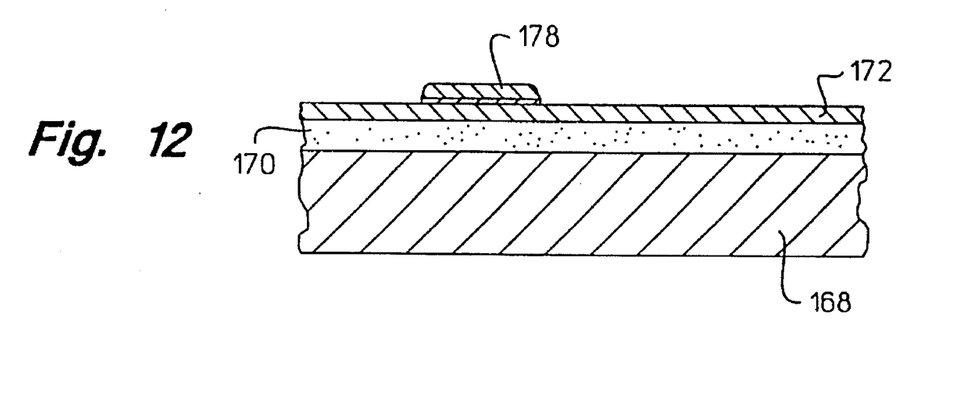
FIG. 12 shows a sectional view of layers of material during the formation of an embodiment of a stage in the fabrication of the microactuator of an ultrasonic probe according to the present invention, showing a layer of magnetic material formed.

In FIG. 11, a layer of photoresist 176 is used to cover areas of the $Si_3N_4$ layer 172 on which deposition of magnetic material is not desired. A NiFe layer 178 of the desired thickness is then electroplated on the portion of the $Si_3N_4$ layer 172, i.e., on the conductive seed film 174, not covered by the photoresist 176. In FIG. 12, after removal of the photoresist and the conductive seed film 174 in selected areas, a NiFe layer of the desired size, thickness, and shape remains on the $Si_3N_4$ layer 172.

Figure 13:
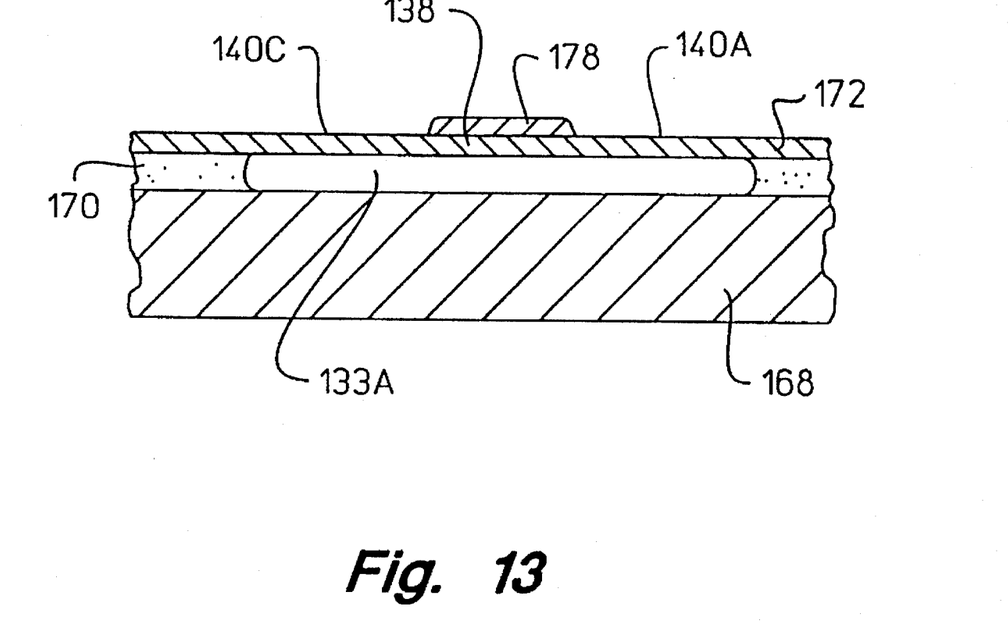
FIG. 13 shows a sectional view of layers of material during the formation of an embodiment of a stage in the fabrication of the microactuator of an ultrasonic probe according to the present invention, showing the formation of a cavity in which the transducer assembly can move pivotally.
Figure 14:
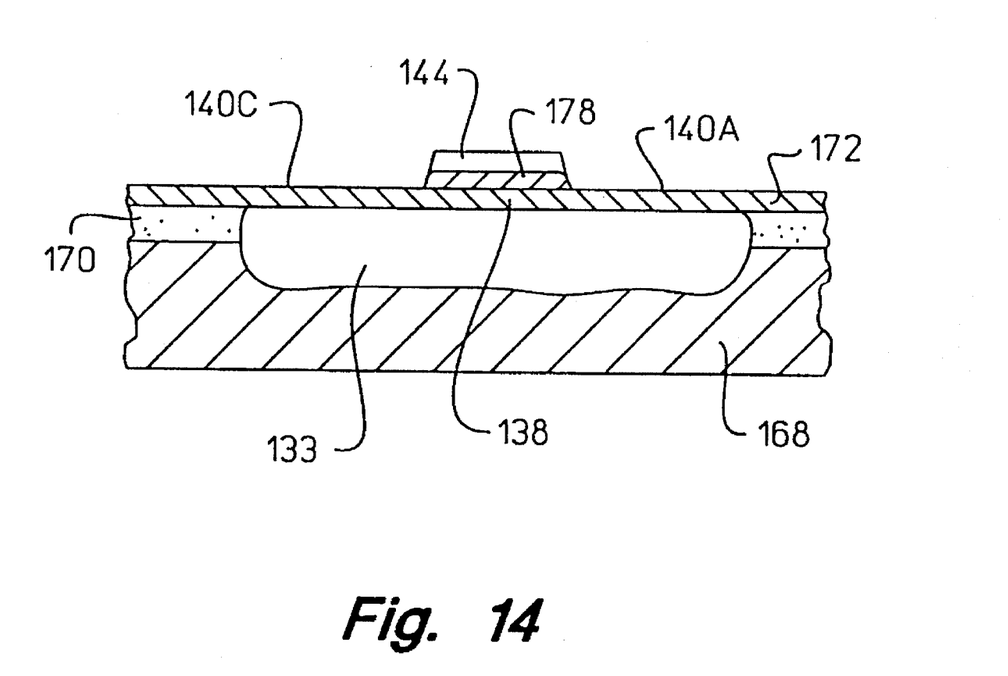
FIG. 14 shows a sectional view of layers of material during the formation of an embodiment of a stage in the fabrication of the microactuator of an ultrasonic probe according to the present invention, showing a transducer disposed on the platform.

In FIG. 13, to shape the substrate 168 defining the cavity 133 (see, also FIG. 6 and FIG. 14), the sacrificial layer 170 beneath the portion of the $Si_3N_4$ layer 172 which is designated to be the platform 138 and the torsion arms is etched by HF. After etching away the selected material of the sacrificial layer 170, the desired silicon substrate area is exposed. This exposed silicon substrate area in the silicon substrate 168 will be etched with an isotropic KOH etching solution to add depth to the cavity 133A. Upon completion of this etch, the cavity 133, as shown in FIG. 14, is formed. A transducer 144 can then be affixed on the platform 138. The conductive pads 148A, 148C and wires 146A, 146C can be used to interface the transducer via cabling 150A, 150C to the controller 114. These steps can be done with commonly known procedures.

Depending on the application of the ultrasonic probe, the size, shape, thickness, and other dimensional characteristics of the microactuator and the transducer can vary to adapt to the application. For example, an intravascular ultrasonic probe will have dimensions much smaller than those of an endoscopic ultrasonic probe. For intravascular ultrasonic probes, the substrate 168 generally can have a thickness of about 100 to 700 µm, preferably about 400 to 500 µm. The platform 138 is preferably rectangular and have a thickness of about 2000 to 10,000 Å, preferably about 4,000 to 9,000 Å. The platform 138 can have a width of about 0.2 to 0.7 mm, preferably about 0.3 to 0.4 mm, and a length of about 0.2 to 2 mm, preferably about 0.5 to 1 mm to provide an adequate surface to support the transducer. The torsion arms 140A, 140C are preferably relatively short compared to the width of the platform so as to result in less stress due to the weight of the platform. However, the torsion arms 140A, 140C should be sufficiently long to allow the pivotal motion of the platform 138 to sweep over a desired angle, which corresponds to the angle swept by the normal of the platform. This angle is less than 180° and typically about 10° to 90°. It preferably is about ±45° with respect to the normal of the platform. Additionally, it is preferred that the width of the platform not be excessive such that the platform does not strike the base of the cavity 133. A wider platform would also require a larger force to turn the platform 138 on the torsion arms 140A, 140C and result in a slower sweep cycle. Generally, the platform 138 can vary from a square shape to a rectangular shape with a width (i.e., the side perpendicular to the torsion arms) to length ratio of about 1:3 to 1:1, preferably about 1:2. Preferably, the length is parallel to the torsional arms 140A, 140C to decrease the force needed to pivot the platform.

As previously stated, the magnetic material is preferably deposited on the upper surface of the platform 138 on both sides of the torsion arms 140A, 140C. If the layer of magnetic material, e.g. NiFe layer 178 is formed such that the N pole is on one side and the S pole is on the other side of the torsion arms 140A, 140C on the surface of the platform 138, a pole of the electromagnet (see, e.g., FIG. 8, electromagnet 154)) below the platform, when a magnetic field is applied by the electromagnet to the platform 138, it will exert an attractive force on the magnetic material on one half of the platform and an repulsive force on the magnetic material on the other half. In this way, the platform 138 is turned about the torsion arms. When the electromagnet reverses polarity, it pivots the platform 138 in the opposite way.

Preferably, to use the surface area of the platform efficiently, the magnetic material occupies substantially all of the upper surface of the platform. Its thickness is preferably less than 25% that of the platform, i.e., the $Si_3N_4$ layer. Various modifications of the above electromagnetic actuation can be contemplated. For example, the pole of the electromagnet can be placed under one side of the platform 138. Another way of actuation is to form the magnetic material on the platform 138 such that the one pole (e.g., the N pole) is on top and the opposite pole is on the bottom and place two poles of an electromagnet each under a different half of the platform.

Preferably, the transducer 144 is mounted on the platform, coveting substantially all of the upper surface of the magnetic material 178 and that of the platform 138 (which is not covered by the magnetic material), to use the platform's surface efficiently. The transducer 144 has the usual electrodes, wires and transducer element, as known in the art for a transducer in ultrasonic probes. Methods of making small transducers for intrabody-cavity applications, such as intravascular applications, are known in the art. As an example, an intravascular ultrasonic probe can have a silicon substrate layer about 500 µm thick. The $Si_3N_4$ platform can be about 9,000 Åthick, 400 µm wide, and about 1,000 µm long. The NiFe layer 178 can be about 10 µm thick and covers essentially all of the upper surface of the platform. The transducer can be made of a layer of piezoelectric material (e.g., PZT lead zirconium titanate.) of about 80 µm thick, a quarter-wave matching layer of graphite about 40 µm thick, and a thick backing material of epoxy and tungsten about 300 µm thick. It can cover essentially all of the upper surface of the platform, therefore covering the NiFe as well. The transducer may also be of quarter-wave material with an appropriate matching layer material such as graphite. Both acoustic matching and backing techniques for making transducers, as well the applicable materials, are known in the art.

The combined thickness of the transducer, the magnetic material, the sacrificial layer, and the platform is thin compared to the length and width thereof. Thus, the combined structure is still generally platform-shaped. The torsion arms 140A, 140C can each be about 5 to 20 µm long. The substrate 168 can have a thickness of about 400 to 500 µm. This will accommodate a cavity 133 of about 300 to 400 µm deep. The sacrificial layer 170 is very thin, generally about 150 to 500 Å. Therefore, the stage 132 has about the same thickness as the substrate 168.

Operation of the Ultrasonic Probe

An ultrasonic probe of the present invention can be inserted into a selected body cavity with standard methods known in the art. For example, generally, an ultrasonic probe is inserted into a body by inserting a sheath with a guidewire into the body, retracting the guide wire from the sheath, and then inserting an ultrasonic probe into the sheath. In the present invention, this method can be used. As an alternative, the ultrasonic probe with a sheath can be inserted into the body directly.

Figure 15:
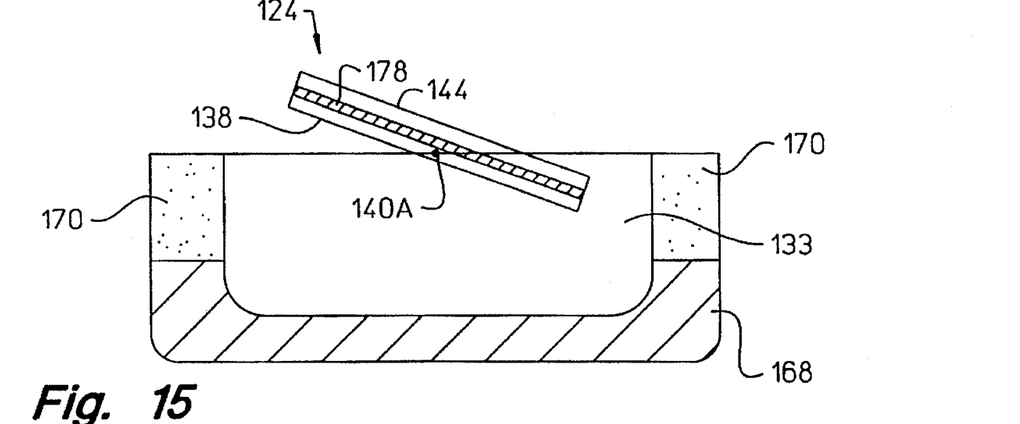
FIG. 15 shows a sectional view of an embodiment of a stage in the ultrasonic probe according to the present invention, showing the platform being pivoted to face a first direction.
Figure 16:
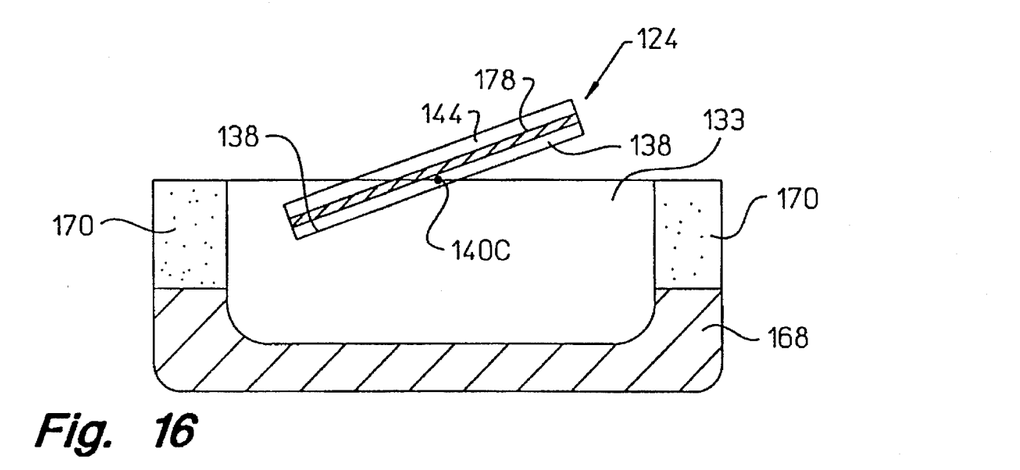
FIG. 16 shows a sectional view of an embodiment of a stage in the ultrasonic probe according to the present invention, showing the platform being pivoted to face a second direction.

When an ultrasonic probe of FIG. 6 or of FIG. 14 is in operation, the controller 114 (see FIG. 1) controls the current flow in the coil in the electromagnet. This causes the electromagnet (not shown in FIG. 6 or FIG. 14) to vary its magnetic field to attract or repel the magnetic material layer 178, which is ferromagnetic. FIG. 15 is a sectional view of the stage 132, with an orientation perpendicular to that of FIG. 14, showing the platform 138 being pivoted such that the plane of the platform forms an angle with the plane of the stage. This position can be achieved, for example, by passing an electrical current through the coil of the electromagnet to energize the electromagnet, thereby repelling one half and attracting the other half of the magnetic material layer 178. When the transducer element, e.g., piezoelectric element, in the transducer 144 is electrically excited, ultrasonic pulses are transmitted normal to the plane of the transducer, i.e., generally normal to the plane of the platform 138. As shown in FIG. 16, when an electric current is passed through the coil of the electromagnet in the opposite direction, the respective halves of the magnetic material layer 178 are attracted and repelled by the electromagnet to pivot the platform 138 to a different angle relative to the plane of the stage 132. As the platform 138 pivots, the transducer assembly 124 rocks on the torsion arms such that the ends of the transducer assembly swing back and forth. By repetitively cycling the pivotal motion of the platform 138, the transducer assembly 124 is swept through an angular range to scan tissues encircling the ultrasonic probe.

A way to bias the platform 138 such that the transducer assembly 124 can be at a desired position when no current passes through the coil of the electromagnet is to include a permanent magnet (not shown in the figures), for example, proximate to the magnetic material layer 178. The size and strength of the permanent magnet is selected such that the constant magnetic field of the permanent magnet exerts a continuous force to bias the platform 138 to a desired position. To scan a large area, the ultrasonic probe may need to be moved periodically so as to move the imaging head (labeled as 106 in FIG. 1) to different locations or orientations. This can be done, for example, by advancing or retracting the imaging head along the longitudinal axis of the catheter and by taming the ultrasonic probe on the longitudinal axis.

Figure 17:
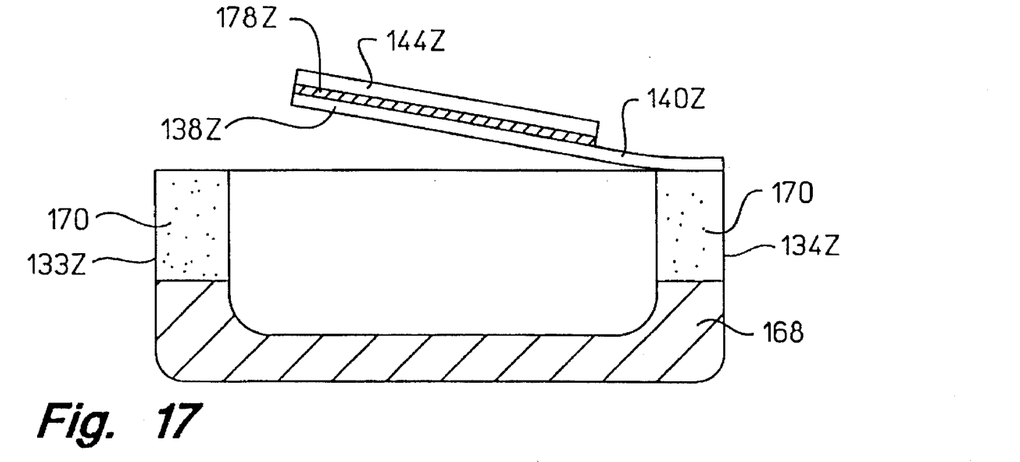
FIG. 17 shows a sectional view of another embodiment of a stage in the ultrasonic probe according to the present invention, showing a flap that is supported at the flap's end.

An alternative embodiment of the ultrasonic probe of the present invention, shown in FIG. 17, includes a flap 138Z linked and supported at one end by support arm(s) 140Z to a wall 134Z surrounding a cavity 133Z. This flap 138Z functions similarly to the platform 138 of FIG. 16 and supports a magnetic material layer 178Z and a transducer 144Z. Such a device can be made, for example, with the method described in Liu, et al. (1995), supra or the method described by Judy and Muller (1995), supra for making microactuators with supporting beams or cantilevers. Again, a permanent magnet can be used to bias the transducer assembly to a desired location when the electromagnet is not activated.

A transducer, e.g., transducer 144, can be used to both transmit and receive ultrasonic signals. As previously stated, the controller 114 is used to control the emission of ultrasonic signals and analyze ultrasonic signals received. Systems for controlling, emission, reception, and analysis of ultrasonic signals are known in the art.

Figure 18:
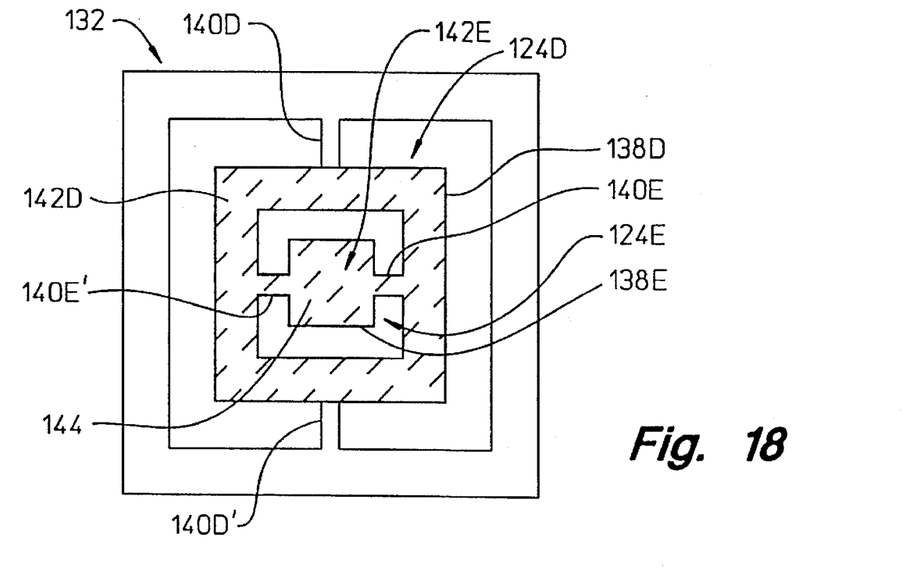
FIG. 18 is a schematic representation of a plan view of a stage according to the present invention, showing a gimbaled transducer assembly.

FIG. 18 illustrates an embodiment in which the stage 132 has a gimbaled transducer assembly 124D in which the a first platform 138D and a second platform 138E each pivots about an axis 90° to each other. The platform 138D rocks on torsion arms 140D and 140D', causing the transducer assembly 124D to rock as a whole. At the center of transducer assembly 124D, a transducer subassembly 124E, which includes the second platform 138E, pivots on torsion arms 140E, 140E'. The transducer subassembly 124E also has a transducer 144 covering the upper surface thereof. The torsion arms 140D, 140D' are aligned with each other but are perpendicular to the torsion arms 140E, 140E', which are aligned with each other. In the transducer subassembly 124E, a layer 142E of magnetic material can be deposited on the second platform 138E, a different pole on each side of the torsion arms 140E, 140E'. Similarly, in the transducer assembly 124D, a layer of magnetic material 142D can be deposited on the first platform 138D outside the transducer subassembly 124E. By applying magnetic fields to the transducer assembly 124D and the transducer subassembly 124E separately by means of electromagnets, the transducer can be pivoted to rock on torsion arms 140D, 140D' and on torsion arms 140E, 140E. One way to apply magnetic fields separately is by means of an electromagnet that has two concentric coils such that the inner coil controls the magnetic field for the transducer subassembly 124E and the outer coil controls the magnetic field of the transducer assembly 124D while canceling out in whole or in part the magnetic field over the transducer subassembly. An alternative way to actuate the pivotal motion of the transducer on the torsion arms 140D, 140D' and on torsion arms 140E, 140E' is by electrostatically attracting different portions of the platforms 138D and 138E by adapting the electrostatic mechanism depicted in FIG. 19, which is described below. This can be done, for example, by positioning a mesa under each half of the platforms 138D and 138E and orchestrating the charging of each mesa to attract various portions of the platforms. Thus, an ultrasonic probe can be made such that it can scan, i.e., to image, three-dimensionally without its head 106 (see FIGS. 1 and 2) being moved. However, it is contemplated that when a large area in the body cavity is to be imaged, the ultrasonic probe would have to be moved to different locations in the body cavity.

Figure 19:
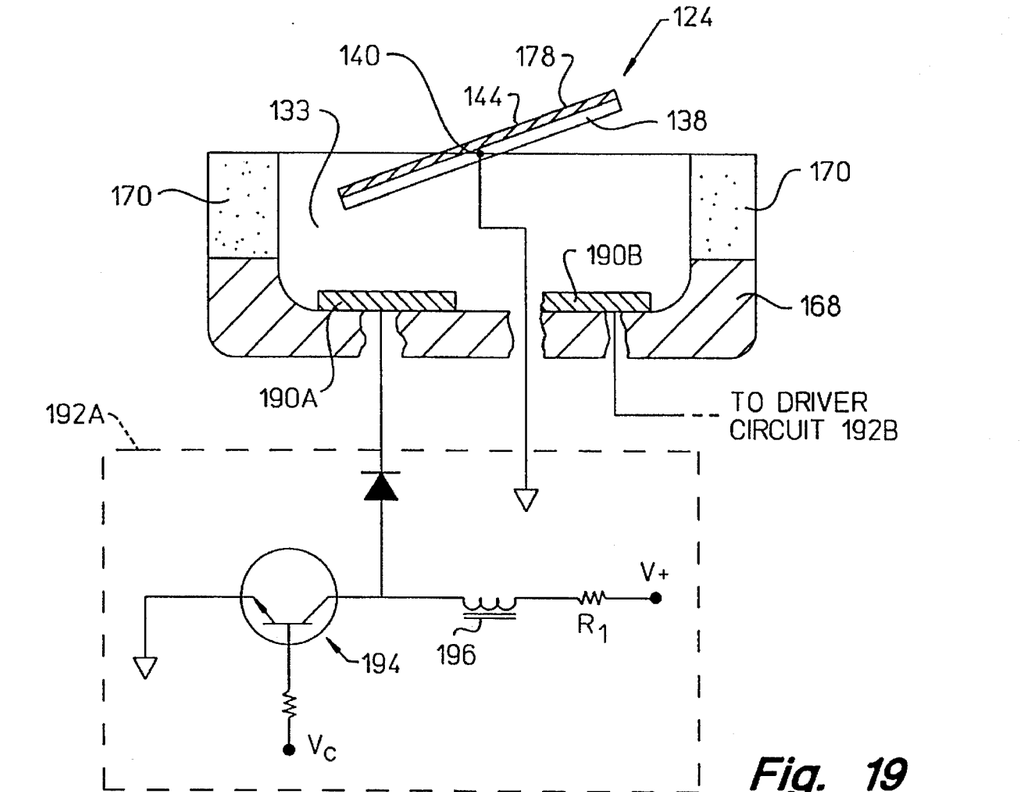
FIG. 19 is a schematic representation of a stage and an electrostatic actuation system according to the present invention.

An alternative to actuation by magnetic force is by electrostatic force. As used herein, the term "electrostatic force" refers to an attracting or repelling force resulting from the electric field of two charged bodies in proximity but not in contact. FIG. 19 illustrates an example. In this embodiment, the construction of the substrate 168, the sacrificial layer 170, the platform 138, and the transducer assembly 124 are similar to that of FIG. 16 except that no magnetic material is deposited on the platform. A metallic conductive mesa 190A, e.g., made with Pd/Ag alloy, is affixed on the substrate 168 underneath the platform 138 on one side of the torsion arm 140. A second metallic conductive mesa 190B is on the substrate on the other side of the torsion arm 140. An electrostatic driver 192A applies an electrostatic force, acting on the mesa 190A to pivot the platform 138.

An example of the electrostatic driver 192A is shown in FIG. 19. However, one skilled in the art will know that other circuitries can be constructed to perform the actuating function. A control voltage $V_c$ drives the transistor 194 by means of a control pulse. When the control voltage is high, the transistor is saturated and the current in the inductor 196 reaches a steady-state value, which depends on the supply voltage, $V_+$ and the resistor $R_1$. When the control voltage is low, the transistor 194 is turned off and the inductor causes charge to be transferred through the diode and onto the mesa 190. The platform 138 and mesa 190A act as plates of a capacitor and the electrostatic force between them causes them to be attracted to each other. The platform 138 returns to its neutral position as charge bleeds off through leakage paths, whereupon the second mesa 190B on the opposite side attracts the platform in the opposite direction. The second mesa 190B is controlled by a driver circuit 192B similar to electrostatic driver 192A such that the drivers coordinate to alternately attract their corresponding halves of the platform 138. Thus, by controlling the applied control voltage, e.g., $V_c$, the platform 138 can be pivoted back and forth. Methods of microfabricating small electrostatic microactuators are known in the art. See, for example, Garabedian et al., "Microfabricated surface plasmon sensing system," *Sensors and Actuators*, A, 43(1994), pp. 202–207 and Richards et al., "Surface-plasmon excitation using a polarization-preserving optical fiber and an index-matching fluid optical cell," *Applied Optics*, 32(16) (1993), pp. 2901–2906.

Although the illustrative embodiments of the device of the present invention and the method of using the device have been described in detail, it is to be understood that the above-described embodiments can be modified by one skilled in the art, especially in sizes and shapes and combination of various described features without departing from the scope of the invention.

What is claimed is:

1. Ultrasonic probe for imaging tissues from inside a patient's body cavity having a wall, the ultrasonic probe being elongated and having a distal end suitable for inserting inside the body cavity and a proximal end opposite the distal end, comprising:

(a) housing having a portion that is substantially transparent to ultrasound, the housing being proximate to the distal end of the ultrasonic probe;

(b) ultrasonic beam transmitting means for transmitting an ultrasonic beam, the means having a pivot able member which directs the ultrasonic beam to a selected direction, the pivot able member being supported by support arm operatively connected in the housing, said support arm by torsion or flexion allowing back and forth pivotal motion of said pivotable member for scanning the ultrasonic beam in the body cavity for imaging; and (c) driver for driving the pivotal motion of the pivot able member, the driver being located proximate to the transducer such that all driving motions occur proximate to the distal end of the ultrasonic probe.

2. The ultrasonic probe according to claim 1 wherein the pivotable member is platform-shaped and has torsion arms which are operatively connected in the housing and are twistable to allow pivotal motion of said pivotable member.

3. The ultrasonic probe according to claim 2 wherein the platform-shaped pivotable member has a transducer to emit the ultrasonic beam.

4. The ultrasonic probe according to claim 2 wherein the pivotable member has a torsion arm supporting the pivotable member, the torsion arm being of a material selected from the group consisting of polysilicon, silicon nitride, and polyimide.

5. The ultrasonic probe according to claim 1 wherein the driver has one of an electrostatic means and an electromagnet for driving the pivotal motion to scan the ultrasonic beam.

6. The ultrasonic probe according to claim 1 wherein the driver has no rotational means for driving a rotational motion in the ultrasonic beam transmitting means to scan the ultrasonic beam.

7. The ultrasonic probe according to claim 1 wherein the ultrasonic beam transmitting means comprises two transducers each having a normal and wherein the normals of the transducers are directed to different directions.

8. The ultrasonic probe according to claim 1 wherein the ultrasonic beam transmitting means includes a generally rectangular surface for emitting the ultrasonic beam, the rectangular surface having a length of about 0.2 mm to 2 mm.

9. The ultrasonic probe according to claim 1 wherein the ultrasonic beam transmitting means includes an ultrasonic reflector which is part of the pivotable member to reflect an ultrasonic beam for a transducer to direct said beam for scanning in the body cavity for imaging.

10. The ultrasonic probe according to claim 1 wherein the pivotable member includes a transducer has a median, such that the pivotable member pivots at about the transducer's median to scan an ultrasonic beam, and the driver includes a layer of magnetic material on the pivotable member such that the pivotable member pivots in response to a varying magnetic field.

11. The ultrasonic probe according to claim 1 wherein the pivotable member is operatively connected to the housing to pivot on at least two fulcrums to scan three-dimensionally.

12. The ultrasonic probe according to claim 1 wherein the transducer has a median, is operatively and pivotally connected in the housing to pivot at about the median to scan an ultrasonic beam, and the driver is adapted to pivot the pivotable member by a varying electrostatic force.

13. The ultrasonic probe according to claim 1 wherein the probe's distal end is of a size insertable into a human blood vessel.

14. The ultrasonic probe according to claim 1 wherein the pivotable member has a surface for a transducer or reflector to be affixed thereon and the dimension of the pivotable member perpendicular to said surface is much smaller than the dimensions of the surface and wherein the support arm is integral with the pivotable member.

15. Ultrasonic probe for imaging tissues from inside a patient's body cavity having a wall, the ultrasonic probe being elongated and having a distal end suitable for inserting inside the body cavity and a proximal end opposite the distal end, comprising:

(a) housing having a portion that is substantially transparent to ultrasound, the housing being proximate to the distal end of the ultrasonic probe;

(b) platform-shaped member with a transducer and having a median, operatively connected and pivotally supported by torsion arms in the housing, pivotable in a back and forth motion at about the median to sweep an ultrasonic beam such that the ultrasonic beam can be reflected by the wall of the body cavity to be received by the ultrasonic probe for imaging the wall of the body cavity; and (c) electromagnetic driver for driving the back and forth pivotal motion of the transducer with a varying magnetic field, the driver being located proximate to the transducer such that all driving motions for driving the pivotal motion occur in the housing proximate to the distal end of the ultrasonic probe, the driver further having a magnetic material connected to the transducer on both sides of the median such that the magnetic material responds to the varying magnetic field of the driver to move the transducer in a rocking manner;

said ultrasonic probe's distal end being of a size insertable into the patient's blood vessel.

16. A method for imaging tissues from inside a patient's body cavity having a wall, comprising:

(a) generating an ultrasonic beam with a transducer inside a housing surrounding the transducer at an inserting end of an ultrasonic probe; and (b) moving a platform-shaped structure back and forth on support arm by flexion or torsion of said support arm in the housing to direct the ultrasonic beam to swingingly scan the ultrasonic beam in the body cavity to image the wall.

17. The method according to claim 16 further comprising moving a reflector pivotally to reflect an ultrasonic beam to scan the ultrasonic beam in a sweeping manner.

18. The method according to claim 16 further comprising mechanically driving the swinging scanning motion of the ultrasonic beam with a driver located proximate to the transducer such that all mechanical driving motions for driving the swinging scanning motion occur proximate to the inserting end of the ultrasonic probe.

19. The method according to claim 16 further comprising pivotally moving the transducer relative to the housing to swingingly scan the ultrasonic beam.

20. The method according to claim 16 further comprising electromagnetically driving the scanning of the ultrasonic beam.

21. The method according to claim 16 further comprising electrostatically driving the scanning of the ultrasonic beam.

22. The method according to claim 16 wherein the step of swingingly scanning the ultrasonic beam comprises electromagnetically actuating a pivotal motion of a platform having a transducer from which ultrasonic energy is transmitted, the platform having a magnetic material affixed thereon to effect the electromagnetic actuation.

23. A method of making an ultrasonic probe for imaging tissues from inside a patient's body cavity having a wall, the ultrasonic probe having an end suitable for inserting into the body cavity, comprising:

(a) providing a housing; and (b) operatively pivotally connecting an ultrasonic beam transmitter having a pivotable member in the housing of the ultrasonic probe at the inserting end thereof such that the pivotable member is supported by support arm at a fulcrum in the housing such that by flexion or torsion of said support arm an ultrasonic beam emitted from a transducer in the transmitter can be scanned for imaging tissues of said body cavity.

24. The method according to claim 23 further comprising positioning a driver for driving the pivotal motion of the pivotable member in the housing, the driver being located proximate to the transducer such that all driving motions that drive the pivotal motion occur proximate to the inserting end of the ultrasonic probe.

* * * * *